United States Patent [19]

Kutter et al.

[11] 4,031,219

[45] June 21, 1977

[54] BIS-HOMOPHTHALIMIDES AND SALTS THEREOF

[75] Inventors: Eberhard Kutter; Volkhard Austel; Wolfgang Eberlein, all of Biberach; Joachim Heider, Warthausen, all of Germany; Walter Kobinger; Christian Lillie, both of Vienna, Austria; Rudolf Kadatz, Biberach, Germany

[73] Assignee: Boehringer Ingelheim GmbH, Ingelheim am Rhein, Germany

[22] Filed: July 13, 1976

[21] Appl. No.: 704,844

[30] Foreign Application Priority Data

July 30, 1975 Germany .......................... 2533986
May 21, 1976 Germany .......................... 2622690

[52] U.S. Cl. .......................... 424/258; 260/281 SP; 260/281 R
[51] Int. Cl.² .............. C07D 217/24; A61K 31/47
[58] Field of Search ............ 424/258; 260/281 SP, 260/281 R

[56] References Cited

UNITED STATES PATENTS 2,271,122  1/1942  Harman .......................... 260/281 R
3,947,451  3/1976  Jonsson et al. ............... 260/281 SP Primary Examiner—Raymond V. Rush
Assistant Examiner—Mark L. Berch
Attorney, Agent, or Firm—Hammond & Littell

[57] ABSTRACT

Compounds of the formula

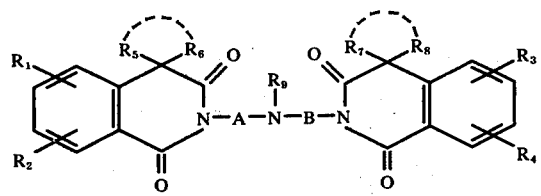

wherein
A and B, which may be identical to or different from each other, are each straight alkylene of 2 to 4 carbon atoms which may have a methyl or phenyl substituent attached thereto, $R_1$, $R_2$, $R_3$ and $R_4$, which may be identical to or different from each other, are each hydrogen, fluorine, chlorine, bromine, hydroxyl, amino, nitro, acetylamino, alkyl of 1 to 3 carbon atoms, alkoxy of 1 to 3 carbon atoms or (alkyl of 1 to 3 carbon atoms)thio, $R_5$, $R_6$, $R_7$ and $R_8$, which may be identical to or different from each other, are each hydrogen, alkyl of 1 to 4 carbon atoms, phenyl-(alkyl of 1 to 4 carbon atoms) or methoxyphenyl-(alkyl of 1 to 4 carbon atoms), or $R_5$ and $R_6$, together with each other, are straight alkylene of 2 to 5 carbon atoms, or $R_7$ and $R_8$, together with each other, are straight alkylene of 2 to 5 carbon atoms, and $R_9$ is hydrogen, alkyl of 1 to 6 carbon atoms or phenyl-(alkyl of 1 to 6 carbon atoms), and non-toxic, pharmaceutically acceptable acid addition salts thereof; the compounds as well as the salts are useful as antiarrhythmics.

10 Claims, No Drawings

BIS-HOMOPHTHALIMIDES AND SALTS THEREOF

This invention relates to novel homophthalimides and non-toxic acid addition salts thereof, as well as to various methods of preparing these compounds.

More particularly, the present invention relates to a novel class of homophthalimides represented by the formula

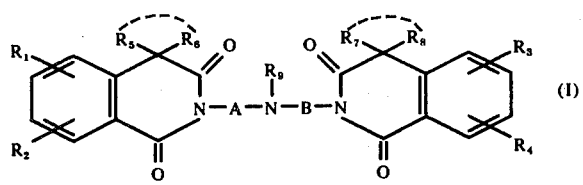

wherein
A and B, which may be identical to or different from each other, are each straight alkylene of 2 to 4 carbon atoms which may have a methyl or phenyl substituent attached thereto, $R_1$, $R_2$, $R_3$ and $R_4$, which may be identical to or different from each other, are each hydrogen, fluorine, chlorine, bromine, hydroxyl, amino, nitro, acetylamino, alkyl of 1 to 3 carbon atoms, alkoxy of 1 to 3 carbon atoms or (alkyl of 1 to 3 carbon atoms)thio, $R_5$, $R_6$, $R_7$ and $R_8$, which may be identical to or different from each other, are each hydrogen, alkyl of 1 to 4 carbon atoms, phenyl-(alkyl of 1 to 4 carbon atoms) or methoxyphenyl-(alkyl of 1 to 4 carbon atoms), or $R_5$ and $R_6$, together with each other, are straight alkylene of 2 to 5 carbon atoms, or $R_7$ and $R_8$, together with each other, are straight alkylene of 2 to 5 carbon atoms, and $R_9$ is hydrogen, alkyl of 1 to 6 carbon atoms or phenyl-(alkyl of 1 to 6 carbon atoms), and non-toxic, pharmaceutically acceptable acid addition salts thereof.

Illustrative and preferred specific embodiments of variables $R_1$ through $R_9$, A and B are the following:

$R_1$ and $R_3$: Hydrogen or methoxy;
$R_2$ and $R_4$: Hydrogen, fluorine, bromine, methyl, methoxy, ethoxy, isopropoxy, methylthio, nitro, amino or acetylamino;
$R_5$, $R_6$, $R_7$ and $R_8$: Hydrogen, methyl, ethyl, propyl, isopropyl, butyl, benzyl, p-methoxy-benzyl or phenyl-propyl;
$R_5$ and $R_6$ together or $R_7$ and $R_8$ together: Ethylene, butylene or pentylene;
$R_9$: Hydrogen, methyl, ethyl, propyl, isopropyl, butyl, n-hexyl, benzyl, phenethyl or phenylpropyl;
A and B: Ethylene, 1-methyl-ethylene, 1-phenyl-ethylene, propylene, 1-methyl-propylene, 3-methyl-propylene or butylene.

The compounds embraced by formula I above may be prepared by the following methods:

METHOD A

By reacting a compound of the formula

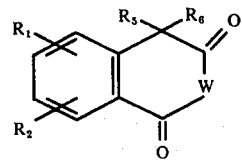

wherein $R_1$, $R_2$, $R_5$ and $R_6$ have the same meanings as in formula I, W is oxygen imino, or a homophthalic acid derivative of the formula

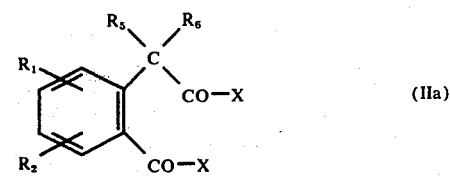

wherein $R_1$, $R_2$, $R_5$ and $R_6$ have the meanings previously defined, and X is halogen, hydroxyl or alkoxy, with an amine of the formula

wherein A, B and $R_9$ have the same meanings as in formula I, and Y is amino or

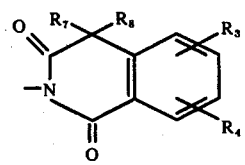

where $R_3$, $R_4$, $R_7$ and $R_8$ have the meanings previously defined.

The reaction may be carried out with the reactants in the molten state; or in the presence of a solvent, such as methylene chloride, ethylene glycol or toluene, and optionally in the presence of a base, such as potassium tert.butylate at temperatures between 0° and 250° C, preferably between 110° and 180° C. Especially preferred is the performance of the reaction in a vessel equipped with a water trap in toluene as the solvent at the boiling point of the toluene.

Furthermore, it should be pointed out that when a compound of the formula II is reacted with a compound of the formula III, the intermediate of the formula

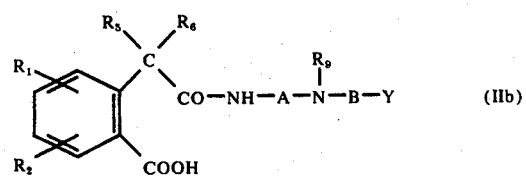

wherein $R_1$, $R_2$, $R_5$, $R_6$, $R_9$, A, B and Y have the meanings previously defined, which is formed may be isolated and subsequently converted into the desired end product under the reaction conditions indicated above.

METHOD B

By reacting an isoquinoline-dione of the formula

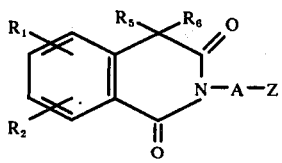

(IV)

wherein $R_1$, $R_2$, $R_5$, $R_6$ and A have the same meaning as in formula I, and Z is a nucleophilically exchangeable substituent, such as halogen, with a homophthalimide of the formula

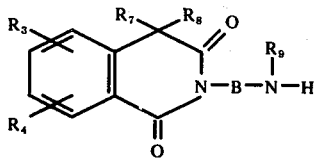

(V)

wherein $R_3$, $R_4$, $R_7$, $R_8$, $R_9$ and B have the same meanings as in formula I.

The reaction is advantageously carried out in the presence of a solvent, such as methanol, ether, tetrahydrofuran, dimethyl formamide, dimethyl sulfoxide, ethylene glycol or benzene, and at temperatures between -50° and 250° C, depending on the reactivity of the substituent Z to be exchanged, but preferably, at the boiling point of the particular solvent which is used. The presence of an acid-binding agent, such as an alcoholate, alkali metal hydroxide or alkali metal carbonate, or of a tertiary organic base, such as pyridine, may be of advantage.

METHOD C

By reacting a carbonyl compound of the formula

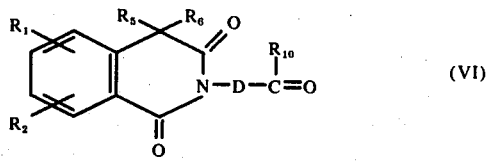

(VI)

wherein $R_1$, $R_2$, $R_5$ and $R_6$ have the same meanings as in formula I, D is straight alkylene of 1 to 3 carbon atoms, optionally substituted by methyl, and $R_{10}$ is hydrogen, methyl or phenyl, with an amine of the formula

(VII)

wherein $R_9$ has the meanings previously defined, and E is hydrogen or a group of the formula

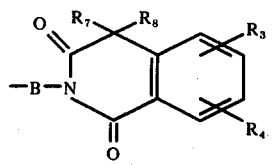

where $R_3$, $R_4$, $R_7$, $R_8$ and B have the meanings previously defined, in the presence of a reducing agent.

The reaction, including the reduction, is preferably carried out in the presence of a solvent, such as methanol, methanol/ammonia, ethanol, ethyl acetate or dioxane, at temperatures between 0° and 100° C, preferably between 40° and 80° C. The reduction is carried out with hydrogen in the presence of a hydrogenation catalyst, for instance, with hydrogen in the presence of palladized charcoal at a hydrogen pressure of 5 atmospheres, or with a complex metal hydride, such as sodium borohydride.

If methods A, B or C yield a compound of the formula I, wherein at least one of substituents $R_5$ to $R_9$ is hydrogen or one of substituents $R_1$ to $R_4$ is hydroxyl, this compound may be converted by means of alkylation into the corresponding alkylated compound of the formula I; and/or if a compound of the formula I is obtained, wherein at least one of substituents $R_1$ to $R_4$ is hydrogen, this compound may be converted by means of nitration into the corresponding nitro-substituted compound of the formula I, which in turn may be converted by means of reduction into the corresponding amino-substituted compound, which in turn may be converted into the corresponding acetyl-amino compound by subsequent acetylation.

The alkylation is preferably carried out with a corresponding alkyl halide or dialkyl sulfate, advantageously in the presence of a solvent, such as ethanol, dimethyl formamide, dimethyl sulfoxide or hexamethyl-phosphoric acid triamide, and in the presence of a base, such as potassium carbonate, sodium hydroxide, sodium ethylate or potassium tert. butylate at temperatures between 20° and 200° C, preferably between 60° and 160° C. If $R_9$ is hydrogen in a compound of the formula I to be methylated, this compound may also be methylated by reaction with formaldehyde/formic acid, advantageously at the boiling point of the reaction mixture.

The compounds embraced by formula I are organic bases and therefore form acid addition salts with inorganic or organic acids. Examples of non-toxic, pharmaceutically acceptable acid addition salts are those formed with hydrochloric acid, hydrobromic acid, sulfuric acid, lactic acid, citric acid, tartaric acid, maleic acid, fumaric acid, 8-chlorotheophylline or the like.

The starting compounds required for methods A to C may be prepared by known methods described in the literature or as indicated in the examples below.

The following examples illustrate the present invention and will enable other skilled in the art to understand it more completely. It should be understood, however, that the invention is not limited solely to the particular examples given below.

EXAMPLE 1

N,N-Bis-[3-(3,4-dihydro-4,4-dimethyl-1,3-dioxo-2(1H)-isoquinolyl)-propyl]-methylamine and its fumarate by method A A mixture consisting of 19 gm (0.1 mol) of 4,4-dimethyl-isochroman-dione-1,3, 3.6 gm (0.025 mol) of bis-(3-aminopropyl)-methylamine and 50 ml of glycol was heated at 180° C for 4 hours. After cooling, 150 ml of an aqueous 10% potassium carbonate solution were added, the mixture was extracted twice with chloroform, and the combined chloroform phases were washed twice with water, dried and evaporated. The residue, the free base reaction product, was dissolved in 100 ml of acetone, the mixed solution was evaporated to a volume of 100 ml, and the crystals formed thereby were suction-filtered off. After recrystallization from water/charcoal, 8.5 gm (56% of theory) of a colorless crystalline product were obtained which had a melting point of 156°–158° C. It was identified to be the compound of the formula

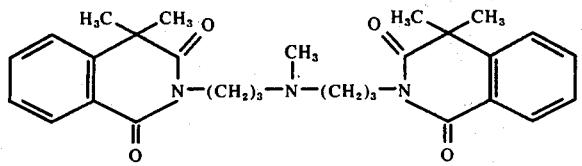
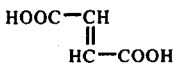

EXAMPLE 2

N,N-Bis-[3-(3,4-dihydro-7-methoxy-4,4-dimethyl-1,3-dioxo-2(1H)-isoquinolyl)-propyl]-amine, m.p. 220°–222° C, was prepared analogous to Example 1 from 22 gm (0.1 mol) of 4,4-dimethyl-7-methoxy-isochroman-dione-1,3 and 3.3 gm (0.025 mol) of bis-(3-aminopropyl)-amine in 50 ml of glycol.

EXAMPLE 3

N,N-Bis-[3-(3,4-dihydro-6,7-dimethoxy-4,4-dimethyl-1,3-dioxo-2(1H)-isoquinolyl)-propyl]-methylamine and its fumarate by method A A mixture consisting of 15 gm (0.06 mol) of 4,4-dimethyl-6,7-dimethoxy-isochroman-dione-1,3 2.9 gm (0.02 mol) of N,N-bis-(3-aminopropyl)-methylamine and and 200 ml of toluene was boiled for 4 hours in a vessel equipped with a water trap. The solvent was then distilled off in vacuo, and the residue was purified on a silicagel column. The fractions containing the desired product were combined and evaporated, and the residue, the free base reaction product, was dissolved in 50 ml of acetone and admixed with a solution of 1.7 gm of fumaric acid in 300 ml of acetone. The mixed solution was evaporated to a volume of 50 ml and ether was added. After about one hour the precipitate which had formed was suction-filtered off and dried, yielding 11.2 gm (77.2% of theory), of the fumarate, m.p. 110° C.

EXAMPLE 4

N,N-Bis-[3-(3,4-dihydro-4,4-dimethyl-1,3-dioxo-2(1H)-isoquinolyl)-propyl]-amine, was prepared analogous to Example 3 from 28.5 gm (0.15 mol) of 4,4-dimethyl-isochroman-dione-1,3 and 6.5 gm (0.05 mol) of N,N-bis-(3-aminopropyl)-amine in 300 ml of toluene. The hydrochloride was precipitated from methanol with ethereal hydrochloric acid. Yield: 13.6 gm (53.1% of theory); m.p. of the hydrochloride: 170°–172° C.

EXAMPLE 5

N,N-Bis-[3-(3,4-dihydro-6,7-dimethoxy-4,4-dimethyl-1,3-dioxo-2(1H)-isoquinolyl)-propyl]-amine, m.p. 215°–216° C (from methanol/acetone), was prepared analogous to Example 3 from 3 gm (0.012 mol) of 4,4-dimethyl-6,7-dimethoxy-isochroman-dione-1,3 and 0.72 gm (0.0055 mol) of N,N-bis-(3-aminopropyl)amine in 150 ml of toluene.

EXAMPLE 6

N-[2-(3,4-Dihydro-4,4-dimethyl-1,3-dioxo-2(1H)-isoquinolylethyl]-N-[3-(3,4-dihydro-4,4-dimethyl-1,3-dioxo-(1H)-isoquinolyl-propyl]-methylamine and its fumarate by method B A mixture consisting of 2.7 gm (0.01 mol) of 4,4-dimethyl-2-(3-chloropropyl)-1,2,3,4-tetrahydro-isoquinolinedione-1,3, 2.8 gm (0.01 mol) of 4,4-dimethyl-2-(2-methylaminoethyl)-1,2,3,4-tetrahydro-isoquinoline-dione-1,3 hydrochloride, 2.24 gm (0.02 mol) of potassium tert.butylate and 30 ml of glycol was heated at 160° C for 5 hours. After cooling, water was added, and the mixture was extracted several times with chloroform. The combined organic extracts were dried, evaporated and purified by column chromatography on silicagel. The residues of the evaporated fractions were dissolved in a small quantity of acetone, the solution was admixed with a solution of 1 gm of fumaric acid in 200 ml of acetone, the mixed solution was evaporated to a volume of about 20 ml and the fumarate was precipitated with ether. Yield: 2.2 gm (37.2% of theory); m.p. 150°–151° C.

EXAMPLE 7

N-[2-(3,4-Dihydro-7-methoxy-4,4-dimethyl-1,3-dioxo-2(1H)-isoquinolyl)-ethyl]-N-[3-(3,4-dihydro-4,4-dimethyl-1,3-dioxo-2(1H)-isoquinolyl)-propyl]-methylamine, was prepared analogous to Example 6 from 2.7 gm (0.01 mol) of 4,4-dimethyl-2-(3-chloro-propyl)-1,2,3,4-tetrahydro-isoquinoline-dione-1,3, 3.1 gm (0.01 mol) of 4,4-dimethyl-7-methoxy-2-(2-methylaminoethyl)-1,2,3,4-tetrahydro-isoquinoline-dione-1,3 hydrochloride and 2.24 gm (0.02 mol) of potassium tert.butylate in 30 ml of glycol. Yield: 1.5 gm (24.1% of theory; m.p. 103°–105° C (decomp.).

EXAMPLE 8

N-[2-(3,4-Dihydro-7-methoxy-4,4-dimethyl-1,3-dioxo-2(1H)-isoquinolyl)-ethyl]-N-[3-(3,4-dihydro-7-methoxy-4,4-dimethyl-1,3-dioxo-2(1H)-isoquinolyl)-propyl]-methylamine was prepared analogous to Example 6 from 3 gm (0.01 mol) of 4,4-dimethyl7-methoxy-2-(3-chloropropyl)-1,2,3,4-tetrahydro-isoquinolinedione-1,3, 3.1 gm (0.01 mol) of 4,4-dimethyl-7-methoxy-2-(2-methylamino-ethyl)-1,2,3,4-tetrahydro-isoquinoline-dione-1,3 hydrochloride and 2.24 gm (0.02 mol) of potassium tert.butylate in 30 ml of glycol. Yield: 1,1 gm (16.9% of theory); m.p. 142°–143° C.

EXAMPLE 9

N-[2-(3,4-Dihydro-4,4-dimethyl-1,3-dioxo-2(1H)-isoquinolyl)-ethyl]-N-[3-(3,4-dihydro-7-methoxy-4,4-dimethyl-1,3-dioxo-2(1H)-isoquinolyl)-propyl]-methylamine was prepared analogous to Example 6 from 3 gm (0.01 mol) of 4,4-dimethyl-7-methoxy-2-(3-chloropropyl)-1,2,3,4-tetrahydro-isoquinoline-dione-1,3, 2.8 gm (0.01 mol) of 4,4-dimethyl-2-(2-methylamino-ethyl)-1,2,3,4-tetrahydro-isoquinoline-dione-1,3 and 2.24 gm (0.02 mol) of potassium tert.butylate in 30 ml of glycol. Yield: 0.7 gm (9.5% of theory); m.p. 158° C.

EXAMPLE 10

N,N-Bis-[3-(3,4-dihydro-4,4-dimethyl-1,3-dioxo-2(1H)-isoquinolyl)-propyl]-ethylamine and its fumarate by method A A mixture consisting of 7.6 gm (0.04 mol) of 4,4-dimethyl-isochroman-dione-1,3, 3.2 gm (0.02 mol) of N,N-bis-(3-aminopropyl)-ethylamine and 100 ml of toluene was refluxed for 4 hours in a vessel equipped with a water trap. The reaction mixture was then evaporated, the residue was purified by column chromatography on silicagel, and the fumarate was precipitated with the calculated quantity of fumaric acid in acetone/ether. Yield: 8.8 gm (71% of theory); m.p. of the fumarate: 141°–142° C.

EXAMPLE 11

N,N-Bis-[3-(3,4-dihydro-7-methoxy-4,4-dimethyl-1,3-dioxo-2(1H)-isoquinolyl)-propyl]-ethylamine was prepared analogous to Example 10 from 8.8 gm (0.04 mol) of 4,4-dimethyl-7-methoxy-isochroman-dione-1,3 and 3.2 gm (0.02 mol) of N,N-bis-(3-amino-propyl)-ethylamine in 100 ml of toluene. Yield: 7 gm (51.4% of theory)- m.p. 141°–143° C.

EXAMPLE 12

N-[3-(3,4-Dihydro-7-methoxy-4,4-dimethyl-1,3-dioxo-2(1H)-isoquinolyl)-propyl]-N-[4-(3,4-dihydro-7-methoxy-4,4-dimethyl-1,3-dioxo-2(1H)-isoquinolyl)-butyl]-propylamine, a viscous oil, was prepared analogous to Example 3 from 16.5 gm (0.07 mol) of 4,4-dimethyl-7-methoxy-isochroman-dione-1,3 and 4.7 gm (0.24 mol) of N-(3-aminopropyl)-N-(4-aminobutyl)-propylamine in 150 ml of toluene. Yield: 7.3 gm (49.2% of theory).

Analysis: Calculated: C-69.01%; H-7.66%; N-7.10%. Found: C-69.00%; H-7.65%; N-7.13%.

EXAMPLE 13

N,N-Bis-[3-(3,4-dihydro-7-methoxy-4,4-dimethyl-1,3-dioxo-2(1H)-isoquinolyl)-propyl]-propylamine, m.p. 161°–162° C, was prepared analogous to Example 10 from 16.5 gm (0.075 mol) of 4,4-dimethyl-7-methoxy-isochroman-dione-1,3 and 4.3 gm (0.025 mol) of N,N-bis-(3-aminopropyl)-propylamine in 150 ml of toluene.

EXAMPLE 14

N-[2-(3,4-dihydro-4,4-dimethyl-1,3-dioxo-2(1H)-isoquinolyl)-ethyl]-N-[2-(3,4-dihydro-6,7-dimethoxy-4,4-dimethyl-1,3-dioxo-2(1H)-isoquinolyl)-ethyl]-methylamine A solution of 10.4 gm (0.1 mol) of sodium hydrogen sulfite in 25 ml of water was added dropwise over a period of 15 minutes to 7.5 ml (0.1 mol) of 40% formalin solution in water, while stirring; subsequently the mixture was then heated at 60° C for 2 hours and added dropwise to 24.6 gm (0.1 mol) of 4,4-dimethyl-2-(2-methylamino-ethyl)-1,2,3,4-tetrahydro-isoquinoline-dione-1,3. After heating it at 50° C for 2 hours, the mixture was cooled, and a solution of 4.9 gm (0.1 mol) of sodium cyanide in 20 ml of water was added. Then the reaction mixture was stirred at 50° C, cooled and extracted twice with chloroform. The combined extracts were dried and evaporated. 26.5 gm (0.0977 mol) of the oil obtained as a residue were hydrogenated in 200 ml of methanolic ammonia in the presence of Raney nickel as a catalyst for 7 hours at 5 atmospheres and 50° C. 28 gm of 4,4-dimethyl-2-[N-methyl-N-(2-aminoethyl)-aminoethyl]-1,2,3,4-tetrahydro-isoquinoline-dione-1,3 were obtained as a highly viscous oil. 5.2 gm (0.018 mol) of the compound thus obtained were reacted with 3.75 gm (0.015 mol) of 4,4-dimethyl-6,7-dimethoxy-isochromandione-1,3 in 100 ml of toluene analogous to Example 10. Yield: 5.9 gm (51.2% of theory); m.p. 122°–123° C (decomp.).

EXAMPLE 15

N,N-Bis-[2-(3,4-dihydro-4,4-dimethyl-1,3-dioxo-2(1H)-isoquinolyl)-ethyl]-methylamine was prepared analogous to Example 14 from 5.8 gm (0.02 mol) of 4,4-dimethyl-2-[N-methyl-N-(2-aminoethyl)-aminoethyl]-1,2,3,4-tetrahydro-isoquinoline-dione-1,3 and 5.7 gm (0.03 mol) of 4,4-dimethyl-isochroman-dione-1,3 in 100 ml of toluene. Yield: 3.3 gm (35.5% of theory; m.p. 106°–107° C.

EXAMPLE 16

N-[2-(3,4-Dihydro-7-methoxy-4,4-dimethyl-1,3-dioxo-2(1H)-isoquinolyl)-ethyl]-N-[2-(3,4-dihydro-4,4-dimethyl-1,3-dioxo-2(1H)-isoquinolyl)-ethyl]-methylamine was prepared analogous to Example 14 from 5.8 gm (0.02 mol) of 4,4-dimethyl-2-[N-methyl-N-(2-aminoethyl)-aminoethyl]-1,2,3,4-tetrahydro-isoquinoline-dione-1,3 and 6.6gm (0.03 mol) of 4,4-dimethyl-7-methoxy-isochroman-dione-1,3 in 100 ml of toluene. Yield: 5.2 gm (43% of theory); m.p. 155°–156° C.

EXAMPLE 17

N-[2-(3,4-Dihydro-7-methoxy-4,4-dimethyl-1,3-dioxo-2(1H)-isoquinolyl)-ethyl]-N-[2-(3,4-dihydro-6,7-dimethoxy-4,4-dimethyl-1,3-dioxo-2(1H)-isoquinolyl)-ethyl]-methylamine was prepared analogous to Example 14 from 6.4 gm (0.02 mol) of 4,4-dimethyl-7-methoxy-2-[N-methyl-N-(2-aminoethyl)-aminoethyl]-1,2,3,4-tetrahydro-isoquinoline-dione-1,3 and 5 gm (0.02 mol) of 4,4-dimethyl-6,7-dimethoxy-isochroman-dione-1,3 in 150 ml of toluene. Yield: 7.3 gm (55% of theory); m.p. 118°–120° C.

EXAMPLE 18

N,N-Bis-[2-(3,4-dihydro-7-methoxy-4,4-dimethyl-1,3-dioxo-2-(1H)-isoquinolyl)-ethyl]-methylamine was prepared analogous to Example 14 from 12.8 gm (0.04 mol) of 4,4-dimethyl-7-methoxy-2-[N-methyl-N-(2-aminoethyl)-aminoethyl]-1,2,3,4-tetrahydro-isoquinoline-dione-1,3 and 13.2 gm (0.06 mol) of 4,4-dimethyl-7-methoxy-isochroman-dione-1,3 in 200 ml of toluene. Yield: 7.8 gm (37.3% of theory); m.p. 150°–151° C (from acetone).

EXAMPLE 19

N,N-Bis-[3-(3,4-dihydro-4,4-dimethyl-1,3-dioxo-2(1H)-isoquinolyl)-propyl]-methylamine and its hydrochloride by method A A mixture consisting of 20.8 gm (0.1 mol) of α,α-dimethyl-homophthalic acid, 3.6 gm (0.025 mol) of N,N-bis-(3-aminopropyl)-methylamine and 50 ml of glycol was heated at 180° C for 4 hours. The reaction mixture was then cooled, admixed with 150 ml of an aqueous 10% potassium carbonate solution, and extracted with chloroform. The extract was washed with water, dried and evaporated. The residue was dissolved in ether, and the hydrochloride was precipitated with ethereal hydrochloric acid. Yield: 9.5 gm (72.2% of theory); m.p. of the hydrochloride: >80° C.

EXAMPLE 20

N,N-Bis-[3-(3,4-dihydro-6,7-dimethoxy-4,4-dimethyl-1,3-dioxo-2(1H)-isoquinolyl)-propyl]-methylamine was prepared analogous to Example 3 from 3.5 gm (0.14 mol) of 4,4-dimethyl-6,7-dimethoxy-isochroman-dione-1,3 and 0.73 gm (0.005 mol) of N,N-bis-(3-aminopropyl)-methylamine in 200 ml of toluene. The hydrochloride was precipitated from ether with ethereal hydrochloric acid. Yield: 2.1 gm (65% of theory); m.p. of the hydrochloride: >70° C.

EXAMPLE 21

N,N-Bis-[3-(3,4-dihydro-4,4-dimethyl-1,3-dioxo-2(1H)-isoquinolyl)-propyl]-amine was prepared analogous to Example 1 from 19 gm (0.1 mol) of 4,4-dimethyl-isochroman-dione-1,3 and 3.3 gm (0.025 mol) of N,N-bis-(3-aminopropyl)-amine. Yield: 8.6 gm (58.1% of theory); m.p. 216° C (from methanol).

EXAMPLE 22

N,N-Bis-[3-(3,4-dihydro-7-methoxy-4,4-dimethyl-1,3-dioxo-2(1H)-isoquinolyl)-propyl]-amine was prepared analogous to Example 3 from 33 gm (0.15 mol) of 4,4-dimethyl-7-methoxy-isochroman-dione-1,3 and 6.5 gm (0.05 mol) of N,N-bis-(3-aminopropyl)-amine in 300 ml of toluene. Yield: 18.3 gm (64% of theory); m.p. 151°-152° C.

EXAMPLE 23

N-[2-(3,4-Dihydro-4,4-dimethyl-1,3-dioxo-2(1H)-isoquinolyl)-ethyl]-N-[3-(3,4-dihydro-4,4-dimethyl-1,3-diono-2(1H)-isoquinolyl)-propyl]-amine and its fumarate by method A A mixture consisting of 19 gm of 4,4-dimethyl-isochroman-dione-1,3 and 4.7 gm of 3-(2-aminoethylamino)-propylamine and 50 ml of ethylene glycol was heated at 160° C for 2 hours. After cooling, the mixture was diluted with water, extracted for several times with chloroform, and the combined chloroform extracts were washed with water and evaporated. The residue was taken up in acetone, and the fumarate was precipitated from this solution with a solution of fumaric acid in acetone. M.p. of the fumarate: 205°-206° C; yield: 20.8 gm (90% of theory).

EXAMPLE 24

N-[3-(3,4-Dihydro-4,4-dimethyl-1,3-dioxo-2(1H)-isoquinolyl)-propyl]-N-[4-(3,4-dihydro-4,4-dimethyl-1,3-dioxo-2(1H)-isoquinolyl)-butyl]-amine was prepared analogous to Example 23 from 9.5 gm of 4,4-dimethyl-isochroman-dione-1,3 and 3.1 gm of N-[4-(3-amino-propylamino)]-butylamine. M.p. of the fumarate: 90°-95° C; yield: 9.6 gm (79% of theory).

EXAMPLE 25

N,N-Bis-[2-(3,4-dihydro-4,4-dimethyl-1,3-dioxo-2(1H)-isoquinolyl)-ethyl]-amine was prepared analogous to Example 23 from 9.5 gm of 4,4-dimethyl-isochroman-dione-1,3 and 2.1 gm of N,N-bis-(2-aminoethyl)-amine. M.p. of the fumarate: 207°-208° C; yield: 9 gm (80% of theory).

EXAMPLE 26

N-[2-(3,4-Dihydro-4,4-dimethyl-1,3-dioxo-2(1H)-isoquinolyl)-ethyl]-N-[4-(3,4-dihydro-4,4-dimethyl-1,3-dioxo-2(1H)-isoquinolyl)-butyl]-amine and its fumarate by method C a. 4,4-Dimethyl-2-(4-aminobutyl)-1,2,3,4-tetrahydro-isoquinoline-1,3-dione 2.56 gm of 4,4-dimethyl-2-(3-cyano-propyl)-1,2,3,4-tetrahydro-isoquinoline-1,3-dione prepared from 4,4-dimethyl-1,2,3,4-tetrahydro-isoquinoline-1,3-dione and 4-chlorobutyric acid nitrile) were dissolved in 50 ml of methanolic ammonia, and the solution was hydrogenated in the presence of 1 gm of Raney nickel at 50° C and 5 atmospheres pressure for 2 hours. The reaction mixture was then diluted with water, acidified and extracted with chloroform. The aqueous phase was made alkaline, extracted with chloroform, and the chloroform extract was evaporated. The residue was used as the starting compound in the following step without purification.

b. 1.5 gm of 4,4-dimethyl-2-(4-aminobutyl)-1,2,3,4-tetrahydro-isoquinoline-1,3-dione and 1.35 gm of [3,4-dihydro-4,4-dimethyl-1,3-dioxo-2(1H)-isoquinolyl]-acetaldehyde (m.p. 81°-82° C, prepared from 4,4-dimethyl-1,2,3,4-tetrahydro-isoquinoline-1,3dione and chloroacetaldehyde-diethylacetal with subsequent acidic saponification) were dissolved in 100 ml of ethanol, and the solution was hydrogenated in the presence of 0.3 gm of 10% palladized coal at 50° C and 5 atmospheres pressure for 10 hours. The product was purified by column chromatography on silicagel (eluant: chloroform/acetone = 19.1) and converted into the fumarate analogous to Example 23. M.p. of the fumarate: 181°-182° C; yield: 1.4 gm (41% of theory).

EXAMPLE 27

N-[2-(3,4-Dihydro-4,4-dimethyl-1,3-dioxo-2(1H)-isoquinolyl)-ethyl]-N-[3-(3,4-dihydro-4,4-dimethyl-1,3-dioxo-2(1H)-isoquinolyl)-propyl]-N-(2-phenylethyl)-amine 5.8 gm of N-[2-(3,4-dihydro-4,4-dimethyl-1,3-dioxo-2(1H)-isoquinolyl)-ethyl]-N-[3-(3,4-dihydro-4,4-dimethyl-1,3-dioxo-2(1H)-isoquinolyl)-propyl]-ammonium fumarate were dissolved in 100 ml of dimethyl formamide, the solution was admixed with 2.8 gm of potassium carbonate and 1.85 gm of 2-phenyl-ethyl bromide, and the mixture was refluxed for 4 hours. After evaporation of the dimethyl formamide, water was added, the aqueous mixture was extracted with chloroform, and purified on silicagel (eluant: chloroform/acetone = 19:1). The product was obtained as a colorless oil. Yield: 3.1 gm (55% of theory).

Analysis: Calculated: C-74.31%, H-6.95%; N-7.43%. Found: C-74.10%; H-7.06%; N-7.41%.

EXAMPLE 28

N,N-Bis-[2-(3,4-dihydro-4-methyl-4-ethyl-1,3-dioxo-2(1H)-isoquinolyl)-ethyl]-amine was prepared analogous to Example 23 from 3.9 gm of 4-methyl-4-ethyl-isochroman-dione-1,3 and 0.79 gm of N,N-bis-(2-amino-ethyl)-amine. The hydrochloride was precipitated from acetone with etheral hydrochloric acid. M.p. of the hydrochloride: above 260° C; yield: 1.7 gm (35% of theory)

Analysis: Calculated: C-65.67%; H-6.69%; N-8.20%; Cl-6.92%. Found: C-65.20%; H-6.60%; N-7.95%; Cl-6.78%.

EXAMPLE 29

N-[3-(3,4-Dihydro-4,4-dimethyl-1,3-dioxo-2(1H)-isoquinolyl)-propyl]-N-[4-(3,4-dihydro-4,4-dimethyl-1,3-dioxo-2(1H)-isoquinolyl)-2-butyl]-amine and its fumarate by method A A mixture consisting of 4.9 gm of [4-(3,4-dihydro-4,4-dimethyl-1,3-dioxo-2(1H)-isoquinolyl)-2-butyl]-(3-aminopropyl)-amine (prepared from methyl-[2-(3,4-dihydro-4,4-dimethyl-1,3-dioxo-2(1H)-isoquinolyl)-ethyl]-ketone and 1,3-diamino-propane by hydrogenation in the presence of palladized coal) and 5.2 gm of 4,4-dimethyl-isochroman-dione-1,3 was heated at 160° C for 2 hours. The reaction product was purified by column chromatograhy on silicagel (eluant: first pure chloroform, then addition of increasing quantities of acetone up to the ratio chloroform/acetone = 9:1), and the fumarate was precipitated as described in Example 23. M.p. of the fumarate: 231°–232° C; yield: 1.7 gm (18% of theory).

EXAMPLE 30

N,N-Bis-[3-(3,4-dihydro-4,4-dimethyl-7-isopropyloxy-1,3-dioxo-2(1H)-isoquinolyl)-propyl]-amine and its fumarate by method A.

A mixture consisting of 4.32 gm of 4,4-dimethyl-7-isoppropyloxy-isochroman-dione-1,3, 0.66 gm of bis-(3-aminopropyl)-amine and 100 ml of toluene was boiled for 1 hour in a vessel equipped with a water trap. The toluene was then evaporated, and the residue was purified by chromatography on silicagel (eluant: chloroform/ethanol = 19:1). The fumarate was obtained as described in Example 23. M.p. of the fumarate: 171°–173° C; yield: 1.2 gm (11% of theory).

EXAMPLE 31

N,N-Bis-[3-(3,4-dihydro-4,4-dimethyl-7-bromo-1,3-dioxo-2(1H)-isoquinolyl)-propyl]-amine was prepared analogous to Example 30 from 4.02 gm of 4,4-dimethyl-7-bromo-isochroman-dione-1,3 and 0.66 gm of N,N-bis-(3-amino-propyl)-amine. M.p. of the fumarate: 214°–216° C; yield: 0.5 gm (4.5% of theory).

EXAMPLE 32

N,N-Bis-[3-(3,4-dihydro-4,4-dimethyl-7-fluoro-1,3-dioxo-2(1H)-isoquinolyl)-propyl]-amine was prepared analogous to Example 30 from 1.8 gm of 4,4-dimethyl-7-fluoro-isochroman-1,3-dione and 0.38 of N,N-bis-(3-amino-propyl)-amine. M.p. of the fumarate: 234°–236° C; yield: 0.31 gm (5.8% of theory).

EXAMPLE 33

N,N-Bis-[3-(3,4-dihydro-1,3-dioxo-2(1H)-isoquinolyl)-propyl]-amine was prepared analogous to Example 30 from 2.44 gm of isochroman-1,3-dione and N,N-bis-(3-amino-propyl)-amine. The hydrochloride was precipitated from acetone with ethereal hydrochloric acid. M.p. of the hydrochloride: 135°–140° C; yield: 0.17 gm (2.5% of the theory).

EXAMPLE 34

N,N-Bis-[3-(3,4-dihydro-1,3-dioxo-2-(1H)-isoquinolyl)-propyl]-methylamine was prepared analogous to Example 30 from 15 gm of isochroman-1,3-dione and N,N-bis-(3-amino-propyl)-methylamine. The hydrochloride was precipitated from acetone with ethereal hydrochloric acid and recrystallized from ethanol. M.p. of the hydrochloride: 202°–205° C; yield: 13.8 gm (32% of theory).

EXAMPLE 35

N,N-Bis-[3-(3,4-dihydro-4,4-diethyl-1,3-dioxo-2(1H)-isoquinolyl)-propyl]-methylamine A mixture consisting of 2.35 gm of bis-[3-(3,4-dihydro-1,3-dioxo-2(1H)-isoquinolyl)-propyl]-methylamine hydrochloride, 5.42 gm of ethyl iodide and 100 ml of ethanol was refluxed while adding a solution of 1.08 gm of sodium hydroxide in 10 ml of water dropwise thereto. The mixture was then stirred at 60° C for 1.5 hours, whereupon the solvent was distilled off, water was added to the residue and the mixture was extracted with ethyl acetate. After purification on a silicagel column (eluant: chloroform/ethanol = 19:1) the hydrochloride was precipitated from acetone with ethereal hydrochloric acid. M.p. of the hydrochloride: 135°–140° C (sintering from 70° C); yield: 0.17 gm (5.8% of theory).

EXAMPLE 36

N-[3-(3,4-Dihydro-4,4-dimethyl-7-methylthio-1,3-dioxo-2(1H)-isoquinolyl)-propyl]-N-[3-(3,4-dihydro-4,4-dimethyl-1,3-dioxo-2(1H)-isoquinolyl)-propyl]-amine was prepared analogous to Example 29 from 3.03 gm of N-[3-(3,4-dihydro-4,4-dimethyl-1,3-dioxo-2(1H)-isoquinolyl)-propyl]-N-(3-amino-propyl)-amine and 2.36 gm of 4,4-dimethyl-7-methylthio-isochroman-dione-1,3. The hydrochloride was precipitated from acetone with ethereal hydrochloric acid. M.p. of the hydrochloride: 116° C (sintering from 74° C); yield: 0.45 gm (8.1% of theory).

EXAMPLE 37

N-[3-(3,4-Dihydro-4,4-dimethyl-7-hydroxy-1,3-dioxo-2(1H)-isoquinolyl)-propyl]-N-[3-(3,4-dihydro-4,4-dimethyl-1,3-dioxo-2(1H)-isoquinolyl)-propyl]-methylamine and its hydrochloride by method A A mixture consisting of 2.4 gm of ethyl 2,2-dimethyl-2-(2-carboxy-4-hydroxy-phenyl)-acetate, 3 gm of N-[3-(3,4-dihydro-4,4-dimethyl-1,3-dioxo-2(1H)-isoquinolyl-propyl]-N-(3-amino-propyl)-methylamine and 20 ml of ethylene gylcol was heated at 160° C for 1.75 hours. Ice water was then added, and the aqueous mixture was extracted with chloroform. After evaporation of the organic extract, the residue was purified on silica gel (eluant: chloroform/ethanol = 19:1), and the hydrochloride was precipitated from acetone with ethereal hydrochloric acid. M.p. 107° C (sintering from 69° C); yield: 3.4 gm (64% of theory).

EXAMPLE 38

N,N-Bis-[3-(3,4-dihydro-4-methyl-4-benzyl-1,3-dioxo-2(1H)-isoquinolyl)-propyl]-amine was prepared analogous to Example 23 from 4 gm of 4-methyl-4-benzyl-isochroman-dione-1,3 and 0.79 gm of N,N-bis-(3-amino-propyl)-amine. M.p. of the fumarate: 170°–172° C; yield: 2.1 gm (38% of theory).

EXAMPLE 39

N,N-Bis-[3-83,4-dihydro-4-methyl-4-n-butyl-1,3-dioxo-2(1H)-isoquinolyl)-propyl]-amine was prepared analogous to Example 23 from 2.75 gm of 4-methyl-4-n-butyl-isochroman-dione-1,3 and 0.62 gm of N,N-bis-(3-amino-propyl)-amine. M.p. of the fumarate: 141°–142° C; yield: 1 gm (25% of theory).

EXAMPLE 40

N-[3-(3,4-Dihydro-4,4,6-trimethyl-1,3-dioxo-2(1H)-isoquinolyl)-propyl]-N-[3-(3,4-dihydro-4,4-dimethyl-1,3-dioxo-2(1H)-isoquinolyl)-propyl]-amine was prepared analogous to Example 29 from 3.03 gm of N-[3-(3,4-dihydro-4,4-dimethyl-1,3-diono-2(1H)-isoquinolyl)-propyl]-N-(3-amino-propyl)-amine and 2.04 gm of 4,4,6-trimethyl-isochroman-dione-1,3. M.p. of the hydrochloride: 203° C (sintering from 145° C); yield: 0.3 gm (5.7% of theory).

EXAMPLE 41

N,N-Bis-[4-(3,4-dihydro-4,4-dimethyl-1,3-dioxo-2(1H)-isoquinoyl)-2-butyl]-amine and its fumarate by method C 5.2 gm of methyl-[2-(3,4-dihydro-4,4-dimethyl-1,3-dioxo-2(1H)-isoquinolyl)-ethyl]-ketone were hydrogenated with 100 ml of methanol and 5 ml of methanolic ammonia in the presence of palladium coal at 70° and 5 atmospheres of pressure for 5 hours. The product was purified on silicagel (eluant: first chloroform, then increasing quantity of acetone up to the ratio chloroform/acetone = 19:1), and the fumarate was precipitated from acetone. M.p. of the fumarate: 188°–189° C; yield: 1.1 gm (18% of theory).

EXAMPLE 42

N-[3-(3,4-Dihydro-4,4-dimethyl-7-ethoxy-1,3-dioxo-2(1H)-isoquinolyl)-propyl]-N-[3-(3,4-dihydro-4,4-dimethyl-1,3-dioxo-2(1H)-isoquinolyl)-propyl]-methylamine 1.3 gm of N-[3-(3,4-dihydro-4,4-dimethyl-7-hydroxy-1,3-dioxo-2(1H)-isoquinolyl)-propyl]-N-[3-(3,4-dihydro-4,4-dimethyl-1,3-dioxo-2(1H)-isoquinolyl)-propyl]-methylamine were dissolved in 10 ml of absolute ethanol, the resulting solution was added to a solution of 0.06 gm of sodium in 10 ml of absolute ethanol, and 0.42 gm of ethyl iodide was added to the mixed solution. The mixture was refluxed for 30 minutes, another 0.42 gm of ethyl iodide was added, and the mixture was refluxed again for 30 minutes. The product was purified on a silicagel column (eluant: chloroform/ethanol = 25:1), and the hydrochloride was precipitated from acetone with ethereal hydrochloric acid. The hydrochloride sintered above 45° C; yield: 0.5 gm (35% of theory).

EXAMPLE 43

N-[3-(3,4-Dihydro-4-methyl-4-(4-methoxy-benzyl)-1,3-dioxo-2(1H)-isoquinolyl)-propyl]-N-[3-(3,4-dihydro-4,4-dimethyl-1,3-dioxo-2(1H)-isoquinolyl)-propyl]-amine 2.4 gm of 4-methyl-4-(4-methoxy-benzyl)-isochroman-dione-1,3 [prepared from methyl 2-methyl-2-(2-methoxycarbonylphenyl)-3-(4-methoxy-phenyl)-propionate by alkaline hydrolysis and subsequent dehydration] and 3 gm of [3-(3,4-dihydro-4,4-dimethyl-1,3-dioxo-2(1H)-isoquinolyl)-propyl]-(3-amino-propyl)-amine were each dissolved in 50 ml of methylene chloride, and the solutions were admixed. After standing for 30 minutes at room temperature the solvent was evaporated, and the residual amide was cyclized by heating at 180° C for 45 minutes. The fumarate was precipitated from acetone. M.p. of the fumarate: 144° C (decomp.); yield: 2.2 gm (39% of theory).

EXAMPLE 44

N-[3-(3,4-Dihydro-4,4-dimethyl-1,3-dioxo-2(1H)-isoquinolyl)-2-propyl]-N-[3-(3,4-dihydro-4,4-dimethyl-1,3-dioxo-2(1H)-isoquinolyl)-pyropyl]-amine was prepared analogous to Example 29 from [3-(3,4-dihydro-4,4-dimethyl-1,3-dioxo-2(1H)-isoquinolyl)-2-propyl]-(3-amino-propyl)-amine and 4,4-dimethyl-isochroman-dione-1,3. M.p. of the fumarate: 168°–169° C.

EXAMPLE 45

N,N-Bis-[3-(3,4-dihydro-4,4-dimethyl-1,3-dioxo-2(1H)-isoquinolyl)-propyl]-n-hexylamine was prepared analogous to Example 27 from 2.6 gm of N,N-bis-[3-(3,4-dihydro-4,4-dimethyl-1,3-dioxo-2(1H)-isoquinolyl)-propyl]-amine and 1 gm of n-hexyl bromide. M.p. of the fumarate: 137°–138° C; yield: 1.7 gm (50% of theory).

EXAMPLE 46

N,N-Bis-[3-(1,2,3,4-tetrahydro-1,3-dioxo-isoquinoline-4-spirocyclohexan-2-yl)-propyl]-methylamine was prepared analogous to Example 35 from 3.6 gm of N,N-bis-[3-(3,4-dihydro-1,3-dioxo-2(1H)-isoquinolyl)-propyl]-methylamine and 4.0 gm of 1,5-dibromopentane. M.p. of the hydrochloride: 183°–185° C; yield: 0.12 gm (2.6% of theory).

EXAMPLE 47

N,N-Bis-[3-(3,4-dihydro-4-isopropyl-1,3-dioxo-2(1H)-isoquinolyl)-propyl]-methylamine was prepared analogous to Example 35 from 4.7 gm of N,N-bis-[3-(3,4-dihydro-1,3-dioxo-2(1H)-isoquinolyl)-propyl]-methylamine and 3.05 gm of isopropyl bromide. M.p. of the hydrochloride: 204°–206° C; yield: 0.12 gm (2.2% of theory).

EXAMPLE 48

N,N-Bis-[3-(1,2,3,4-tetrahydro-1,3-dioxo-isoquinoline-4-spirocyclopropan-2-yl)-propyl]-methylamine was prepared analogous to Example 35 from 3.6 gm of N,N-bis-[3-(3,4-dihydro-1,3-dioxo-2(1H)-isoquinolyl)-propyl]-methylamine and 3.3 gm of 1,2-dibromo-ethane. M.p. of the hydrochloride: 192°–196° C; yield: 0.05 gm (1.3% of theory).

EXAMPLE 49

N,N-Bis-[3-(3,4-dihydro-4,4-dimethyl-1,3-dioxo-2(1H)-isoquinolyl)-propyl]-N-(3-phenyl-propyl)-amine and its hydrochloride A solution of 1.8 gm of 3-phenyl-bromopropane and 0.96 gm of sodium hydroxide in 20 ml of water were simultaneously added in small portions to a solution of 2.56 gm of N,N-bis-[3-(3,4-dihydro-4,4-dimethyl-1,3-dioxo-2(1H)-isoquinolyl)-propyl]-amine hydrochloride in 100 ml of ethanol at 70° C. After 16 hours of standing, the mixture was poured into water, the aqueous mixture was extracted with ethyl acetate, the extract was evaporated and the residue was purified on silicagel (eluant: chloroform/ethanol = 19:1). The hydrochloride was precipitated from ethyl acetate with ethereal hydrochloric acid. M.p. of the hydrochloride: 135° C; yield: 0.13 gm (4.2% of theory).

EXAMPLE 50

N-[3-(3,4-dihydro-4-methyl-4-(3-phenyl-propyl)-1,3-dioxo-2(1H)-isoquinolyl)-propyl]-N-[3-(4,4-dimethyl-1,3-dioxo-3,4-dihydro-2(1H)-isoquinolyl)-propyl]-amine was prepared analogous to Example 43 from 3 gm of 4-methyl-4-(3-phenyl-propyl)-isochroman-dione-1,3 and 3.1 gm of N-[3-(3,4-dihydro-4,4-dimethyl-1,3-dioxo-2(1H)-isoquinolyl)-propyl]-N-(3-amino-propyl)-amine. M.p. of the fumarate: 158°–163° C; yield: 3.7 gm (52% of theory).

EXAMPLE 51

N,N-Bis-[3-(3,4-dihydro-4,4-dimethyl-7-acetamino-1,3-diomo-2(1H)-isoquinolyl)-propyl]-methylamine and its hydrochloride 3.25 gm of N,N-bis-[3-(3,4-dihydro-4,4-dimethyl-7-amino-1,3-dioxo-2(1H)-isoquinolyl)-propyl]-methylamine trihydrochloride were suspended in 70 ml of acetic acid anhydride, and the suspension was stirred at room temperature for 2 hours. The mixture was then poured over ice, was made alkaline with ammonia, extracted with chloroform, the extract was evaporated, and the residue was purified by column chromatography on silicagel (eluant: chloroform/methanol = 9:1). The hydrochloride was precipitated from ethanol with ethereal hydrochloride acid and recrystallized from isopropanol. M.p. of the hydrochloride: 175° C; yield: 1.8 gm (54% of theory).

EXAMPLE 52

N,N-Bis-[3-(3,4-dihydro-4,4-dimethyl-7-amino-1,3-dioxo-2(1H)-isoquinolyl)-propyl]-methylamine and its trihydrochloride 5.3 gm of N,N-bis-[3-(3,4-dihydro-4,4-dimethyl-7-nitro-1,3-dioxo-2(1H)-isoquinolyl)-propyl]-methylammonium nitrate were dissolved in 100 ml of methanol, 10 ml of methanolic hydrochloric acid and 0.6 gm of 10% palladized coal were added, and the mixture was reduced with hydrogen at 5 atmospheres pressure and at room temperature. The catalyst was suction-filtered off, the solvent was removed from the filtrate, and the residue was taken up in water. The aqueous solution was extracted with methylene chloride, made alkaline with ammonia and again extracted with methylene chloride. The methylene chloride phase was evaporated, the residue was dissolved in ethanol, and the trihydrochloride was precipitated with ethereal hydrochloric acid. M.p. of the trihydrochloride: 225° C; yield: 3.25 gm (63% of theory).

EXAMPLE 53

N,N-Bis-[3-(3,4-dihydro-4,4-dimethyl-7-nitro-2(1H)-isoquinolyl)-propyl]-methylamine nitrate 5 gm of N,N-bis-[3-(3,4-dihydro-4,4-dimethyl-1,3-dioxo-2(1H)-isoquinolyl-propyl]-methylammonium fumarate were added to 50 ml of fuming nitric acid at −20° to −30° C, and the mixture was stirred at −25° C for 40 minutes. The resulting solution was poured over ice, and the precipitated nitrate was suction-filtered off. M.p. of the nitrate: 135° C; yield: 5.3 gm (100% of theory).

EXAMPLE 54

N,N-Bis-[3-(3,4-dihydro-4,4-dimethyl-7-nitro-1,3-dioxo-2(1H)-isoquinolyl)-propyl]-amine nitrate was prepared analogous to Example 53 from 10 gm of N,N-bis-[3-(3,4-dihydro-4,4-dimethyl-1,3-dioxo-2(1H)-isoquinolyl)-propyl]-amine hydrochloride. M.p. of the nitrate: 197° C; yield: 10.2 gm (83% of theory).

EXAMPLE 55

N,N-Bis-[3-(3,4-dihydro-4,4-dimethyl-7-amino-1,3-dioxo-2(1H)-isoquinolyl)-propyl]-amine and its monohydrochloride was prepared analogous to Example 52 from N,N-bis-[3-(3,4-dihydro-4,4-dimethyl-7-nitro-1,3-dioxo-2(1H)-isoquinolyl)-propyl]-ammonium nitrate. M.p. of the monohydrochloride: above 300° C (sintering from 285° C); yield: 1 gm (41% of theory) (monohydrochloride).

EXAMPLE 56

N,N-Bis-[3-(3,4-dihydro-4,4-dimethyll-1,3-dioxo-2(1H)-isoquinolyl)-propyl]-amine and its hydrochloride by method A A mixture consisting of 0.2 gm of 2,4,4-trimethyl-1,2,3,4-tetrahydro-isoquinoline-dione-1,3 and 0.3 gm of N-[3-(3,4-dihydro-4,4-dimethyl-1,3-2(1H)-isoquinolyl)-propyl]-N-(3-amino-propyl)-amine was heated at 160° C for 4 hours, and the reaction mixture was purified on a silicagel column (eluant: chloroform/methanol = 9:1). The hydrochloride was precipitated from methanol with ethereal hydrochloric acid. M.p. of the hydrochloride: 170°–172° C; yield: 0.15 gm (29% of theory).

EXAMPLE 57

N,N-Bis-[3-(1,2,3,4-tetrahydro-1,3-dioxo-isoquinoline-4-spiro -cyclopentan-2-yl)-propyl]-methylamine was prepared analogous to Example 43 from 0.85 gm of isochroman-4-spiro-cyclopentane-dione- 1,3 and 0.24 gm of N,N-bis-(3-amino-propyl)-methyl-amine, M.p. of hydrochloride: 127°–132° C; yield: 0.07 gm (2.9% of theory).

EXAMPLE 58

N,N-Bis-[3-(3,4-dihydro-4,4-dimethyl-1,3-dioxo-2(1H)-isoquinolyl)-propyl]-benzylamine was prepared analogous to Example 49 from 5.12 gm of N,N-bis-[3-(3,4-dihydro-4,4-dimethyl-1,3-diomo-2(1H)-isoquinolyl)-propyl]-amine hydrochloride and 1.75 gm of benzyl bromide with sodium ethylate. M.p. 108° C; yield: 3.7 gm (65% of theory).

EXAMPLE 59

N-[2-(3,4-Dihydro-4,4-dimethyl-1,3-dioxo-2(1H)-isoquinolyl)-1-phenyl-ethyl]-N-[3-(3,4-dihydro-4,4-dimethyl-1,3-diomo-2(1H)-isoquinolyl)-propyl]-amine was prepared analogous to Example 26(b) from 0.7 gm of 1,2,3,4-tetrahydro-4,4-dimethyl-2-(2-amino-2-phenyl-ethyl)-isoquinoline-dione-1,3 and 0.6 gm of 3-(3,4-dihydro-4,4-dimethyl-1,3-dioxo-2(1H)-isoquinolyl)-propionaldehyde. The product was obtained as a colorless oil. Yield: 0.3 gm (22% of theory).

Analysis: Calculated C-73.71%; H-6.55%; N-7.82%. Found: C-72.90%; H-6.94%; N-7.61%.

The compounds of the present invention, that is, those embraced by formula I above and their non-toxic, pharmaceutically acceptable acid addition salts, have useful pharmacodynamic properties. More particularly, they exhibit antiarrhythmic activity in warm-blooded animals, such as mice, and are therefore useful for the treatment of cardiac arrhythmia.

The antiarrhythmic activity and the toxicity of the compounds of this invention was ascertained by the test methods described below. Representative results of these tests are shown in the tables, where A = N,N-bis-[3-(3,4-dihydro-4,4-dimethyl-1,3-dioxo-2-(1H)-isoquinolyl)-propyl]-methylamine,
B = N,N-bis-[3-(3,4-dihydro-4,4-dimethyl-1,3-dioxo-2(1H)-isoquinolyl)propyl]-amine,
C = N,N-bis-[3-(3,4-dihydro-4,4-dimethyl-1,3-dioxo-2(1H)-isoquinolyl)-propyl]-ethylamine,
D = N-[2-(3,4-dihydro-7-methoxy-4,4-dimethyl-1,3-dioxo-2-(1H)-isoquinolyl)-ethyl]-N-[3-(3,4-dihydro-4,4-dimethyl-1,3-dioxo-2(1H)-isoquinolyl)-propyl]-methylamine,
E = N-[2-(3,4-dihydro-4,4-dimethyl-1,3-dioxo-2(1H)-isoquinolyl)-ethyl]-N-[3-(3,4-dihydro-7-methoxy-4,4-dimethyl-1,3-dioxo-2-(1H)-isoquinolyl)-propyl]-methylamine,
F = N,N-bis-[2-(3,4-dihydro-4,4-dimethyl-1,3-dioxo-2(1H)-isoquinolyl)-ethyl]-methylamine,
G = N-[2-(3,4-dihydro-4,4-dimethyl-1,3-dioxo-2(1H)-isoquinolyl)-ethyl]-N-[3-(3,4-dihydro-4,4-dimethyl-1,3-dioxo-2(1H)-isoquinolyl)-propyl]-amine,
H = [3-(3,4-dihydro-4,4-dimethyl-1,3-dioxo-2(1H)-isoquinolyl)-propyl]-[4-(3,4-dihydro-4,4-dimethyl-1,3-dioxo-2(1H)-isoquinolyl)-butyl]-amine,
I = Bis-[2-(3,4-dihydro-4,4-dimethyl-1,3-dioxo-2(1H)-isoquinolyl)-ethyl]-amine, and
J = [2-(3,4-dihydro-4,4-dimethyl-1,3-dioxo-2(1H)-isoquinolyl)-ethyl]-[4-(3,4-dihydro-4,4-dimethyl-1,3-dioxo-2(1H)-isoquinolyl)-butyl]-amine.

1. Effect on the effective refractory period of the isolated electrically stimulated left auricle of the guinea pig

Method

Guinea pigs of both sexes were killed by a blow on the neck. After opening the thorax, the heart was quickly removed and transferred to a Tyrode solution (37° C). The auricles were therein dissected, and only the left auricles were used. Electrical stimulation was performed by a Grass Stimulator, S4G, with square wave impulses of 1 millisecond duration and a stimulation voltage of 12 V. The auricles were suspended in Tyrode solution at 37° C containing NaCl: 136.8 mval/liter; KCl: 2.68 mval/liter; $MgCl_2$: 0.2625 mval/liter; $NaH_2PO_4$: 0.417 mval/liter; $NaHCO_3$: 11.9 mval/liter; $CaCl_2$: 1.8 mval/liter; glucose: 3 gm. The solution was continuously oxygenated with 98% $O_2$ and 2% $CO_2$. The isometric contractions were measured with a force-displacement transducer and recorded on a Grass-polygraph (P5).

The auricles were stimulated with 0.5 Hz. The maximum driving frequency was measured by increasing the stimulation rate every 10 seconds by 1 Hz. Measurements were performed three times every 5 minutes before and 5 and 10 minutes after the addition of the test compound. During the rest periods between the measurements the stimulation frequency was 0.5 Hz. The effect of the compound was calculated as the mean change of maximum driving frequency 5 and 10 minutes after adding the compound. The compound was tested by increasing the concentration to obtain dose-response-curves and to calculate the $EC_{50}$.

Principle

The maximum driving frequency is measured by increasing the stimulation rate. When the interval between two stimuli is shortened, a stimulation rate is reached at which every second stimulation falls into the refractory period of the foregoing contraction and will not be answered with a contraction. Thus, the maximum driving frequency is a measure for the effective refractory period. Compounds which reduce the maximum driving frequency prolong the refractory period.

Results

From the dose-response-curves the following concentrations, which reduce the maximum driving frequency by 50%, were graphically determined:

TABLE I

| Compound | $EC_{50}$ in µg/ml |
|---|---|
| A | 5.5 |
| B | 8.0 |
| C | 2.0 |
| D | 4.2 |
| G | 2.7 |
| H | 10.0 |
| I | 2.2 |
| J | 1.8 |

2. Antiarrhythmic activity against chloroform-induced ventricular fibrillation in mice

Method

Upon putting a mouse into a chloroform-saturated atmosphere, the animal is anaesthetized after 40 seconds, the spontaneous respiration stops, and after 20 seconds more, gasping respiration is seen.

When the respiration is completely suppressed, the mouse is taken out of the chloroform-atmosphere, the thorax is opened and the heart is quickly exposed to observe the heart movement. During 1 minute after opening the thorax spontaneous ventricular fibrillation can be obtained in nearly all the animals or can be induced in others by touching the heart with tweezers.

Pretreatment with antiarrhythmic compounds reduces the number of animals which show fibrillations in a dose-dependent way. The dose which reduces the number of animals by 50% ($ED_{50}$) is calculated by means of dose-response-curves, and the standard error is determined [Miller, L.C. and Tainter, M.L., Proc. Soc. Exp. Biol. Med. 57, 261 (1944)].

The tests were performed on male mice having a body weight of 20–25 gm. Each dose was tested on 10 animals.

The compounds were administered intravenously 1 minute before inducing ventricular fibrillation.

The following results were obtained:

TABLE II

| Compound | $ED_{50}$ mgm/kg i.v. |
|---|---|
| A | 1.2 |
| B | 2.5 |
| C | 0.5 |
| D | 3.6 |
| F | 4.6 |
| G | 4.7 |
| H | 3.0 |

TABLE II-continued

| Compound | ED$_{50}$ mgm/kg i.v. |
|---|---|
| I | 4.7 |
| J | 2.8 |

3. Acute toxicity

The acute toxicity of the test compounds was determined in mice (observation time: 14 days) after oral and/or intravenous application. The LD$_{50}$ was calculated from the percentage of animals which died within the observation time after administration of various doses [see J. Pharmacol. exp. Therap. 96, 99 (1949)].

TABLE III

| Compound | LD$_{50}$ | |
|---|---|---|
| B | 123 | mgm/kg p.o. |
| I | 15.0 | mgm/kg i.v. |
|   | 315 | mgm/kg p.o. |
| J | 10.5 | mgm/kg i.v. |
|   | 210 | mgm/kg p.o. |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antiarrhythmic dosage unit of the compounds of the present invention is from 0.41 to 0.83 mgm/kg body weight.

The following examples illustrate a few pharmaceutical dosage unit compositions comprising a compound of the present invention as an active ingredient and represent the best modes comtemplated of putting the invention into practical use. The parts are by weight unless otherwise specified.

EXAMPLE 60

Tablets

The tablet composition is compounded from the following ingredients:

| | | |
|---|---|---|
| N,N-Bis-[3-(3,4-dihydro-4,4-dimethyl-1,3-dioxo-2(1H)-isoquinolyl)-propyl]-methylamine | | 50.0 parts |
| Lactose | | 100.0 parts |
| Polyvinylpyrrolidone | | 5.0 parts |
| Carboxymethyl cellulose | | 19.0 parts |
| Magnesium stearate | | 1.0 parts |
| | Total | 175.0 parts |

Preparation

The methylamine derivative is intimately admixed with the lactose and the polyvinylpyrrolidone, the mixture is granulated by moist screening through a 1.5 mm-mesh screen, the granulate is dried at 50° C in a circulating air dryer, and the dry granulate is again passed through a 1.0 mm-mesh screen. The magnesium stearate and the carboxymethyl cellulose are then blended into the granulate, and the resulting composition is compressed into 175 mgm-tablets. Each tablet contains 50 mgm of the methylamine compound and is an oral dosage unit composition with effective antiarrhythmic action.

EXAMPLE 61

Coated pills

The pill core composition is compounded from the following ingredients:

| | | |
|---|---|---|
| N,N-Bis-[3-(3,4-dihyro-4,4-dimethyl-1,3-dioxo-2(1H)-isoquinolyl)-propyl]-methylamine | | 25.0 parts |
| Corn starch, dried | | 45.0 parts |
| Soluble starch | | 2.0 parts |
| Carboxymethyl cellulose | | 7.0 parts |
| Magnesium stearate | | 1.0 parts |
| | Total | 80.0 parts |

Preparation

The methylamine derivative and the corn starch are intimately admixed with each other, the mixture is moistened with an aqueous solution of the soluble starch and granulated through a 1.0 mm-mesh screen, the granulate is dried at 50° C in a circulating air dryer, and the dry granulate is again passed through the above screen. The carboxymethyl cellulose and the magnesium stearate are then blended into the granulate, and the resulting composition is compressed into 80 mgm-pill cores which are subsequently coated with a thin shell consisting essentially of sugar and talcum. Each coated pill contains 25 mgm of the methylamine derivative and is an oral dosage unit composition with effective antiarrhythmic action.

EXAMPLE 62

Suppositories

The suppository composition is compounded from the following ingredients:

| | | |
|---|---|---|
| N,N-Bis-[3-(3,4-dihydro-4,4-dimethyl-1,3-dioxo-2(1H)-isoquinolyl)-propyl]-methylamine | | 50.0 parts |
| Suppository base (e.g. cocoa butter) | | 1650.0 parts |
| | Total | 1700.0 parts |

Preparation

The suppository base is melted, cooled to 38° C, and the pulverized methylamine derivative is homogeneously dispersed therein. The composition is then cooled to 35° C, and 1700 mgm-portions thereof are poured into cooled suppository molds and allowed to harden therein. Each suppository contains 50 mgm of the methylamine derivative and is a rectal dosage unit composition with effective antiarrhythmic action.

EXAMPLE 63

Hypodermic solution

The solution is compounded from the following ingredients:

| | | |
|---|---|---|
| N,N-Bis-[3-(3,4-dihydro-4,4-dimethyl-1,3-dioxo-2(1H)-isoquinolyl)-propyl]-methylamine | | 50.0 parts |
| Sorbitol | | 250.0 parts |
| Distilled water | q.s.ad | 500.0 parts by vol. |

Preparation

The methylamine derivative and the sorbitol are dissolved in a sufficient amount of distilled water, and the solution is diluted to the indicated volume with additional distilled water and then filtered until free from suspended particles. The filtrate is filled into 5 cc-ampules which are then sterilized for 20 minutes at 120° C and sealed. Each ampule contains 50 mgm of the methylamine derivative, and its contents are an injectable solution with effective antiarrhythmic action.

EXAMPLE 64

Drop solution

The solution is compounded from the following ingredients:

| | | |
|---|---|---|
| N,N-Bis-[3-(3,4-dihydro-4,4-dimethyl-1,3-dioxo-2(1H)-isoquinolyl)-propyl]-methylamine | 5.0 | parts |
| Methyl p-hydroxybenzoate | 0.035 | parts |
| Propyl p-hydroxybenzoate | 0.015 | parts |
| Anise oil | 0.05 | parts |
| Menthol | 0.06 | parts |
| Saccharin sodium | 1.0 | parts |
| Glycerin | 10.0 | parts |
| Ethanol | 40.0 | parts |
| Distilled water q.s.ad | 100.0 | parts by vol. |

Preparation

The p-hydroxy-benzoates are dissolved in the ethanol, and the anise oil and the menthol are added thereto (solution I). The methylamine derivative, the glycerin and the saccharin sodium are dissolved in the distilled water (solution II). Solution II is added to solution I, and the mixed solution is filtered until clear. 5 ml of the filtrate contain 25 mgm of the methylamine derivative and are an oral dosage unit composition with effective antiarrhythmic action.

Analogous results were obtained when any one of the other compounds embraced by formula I or a non-toxic, pharmaceutically acceptable acid addition salt thereof was substituted for the particular methylamine derivative in Examples 60 through 64. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

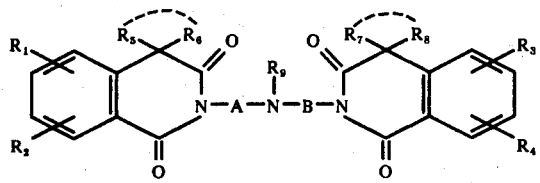

wherein
A and B are each straight alkylene of 2 to 4 carbon atoms which may have a methyl or phenyl substituent attached thereto,
$R_1$, $R_2$, $R_3$ and $R_4$ are each hydrogen, fluorine, chlorine, bromine, hydroxyl, amino, nitro, acetylamino, alkyl of 1 to 3 carbon atoms, alkoxy of 1 to 3 carbon atoms or (alkyl of 1 to 3 carbon atoms) thio,
$R_5$, $R_6$, $R_7$ and $R_8$ are each hydrogen, alkyl of 1 to 4 carbon atoms, phenyl-(alkyl of 1 to 4 carbon atoms) or methoxyphenyl-(alkyl of 1 to 4 carbon atoms), or
$R_5$ and $R_6$, together with each other, are straight alkylene of 2 to 5 carbon atoms, or
$R_7$ and $R_8$, together with each other, are straight alkylene of 2 to 5 carbon atoms, and
$R_9$ is hydrogen, alkyl of 1 to 6 carbon atoms or phenyl-(alkyl of 1 to 6 carbon atoms),
or a non-toxic, pharmaceutically acceptable acid addition salt thereof.

2. A compound of claim 1,
where A and B are each straight alkylene of 2 to 4 carbon atoms which may have a methyl or phenyl substituent attached thereto,
$R_1$ is hydrogen,
$R_2$ and $R_4$ are each hydrogen, fluorine, chlorine, bromine, hydroxyl, amino, nitro, acetylamino, alkyl of 1 to 3 carbon atoms, alkoxy of 1 to 3 carbon atoms or (alkyl of 1 to 3 carbon atoms) thio,
$R_3$ is hydrogen or methoxy,
$R_5$, $R_6$, $R_7$ and $R_8$ are each hydrogen, alkyl of 1 to 4 carbon atoms, phenyl-(alkyl of 1 to 4 carbon atoms) or methoxyphenyl-(alkyl of 1 to 4 carbon atoms), or
$R_5$ and $R_6$, together with each other, are straight alkylene of 2 to 5 carbon atoms, or
$R_7$ and $R_8$, together with each other, are straight alkylene of 2 to 5 carbon atoms, and
$R_9$ is hydrogen, alkyl of 1 to 6 carbon atoms or phenyl-(alkyl of 1 to 6 carbon atoms).

3. A compound of claim 1,
wherein A and B are each straight alkylene of 2 to 4 carbon atoms which may have a methyl substituent attached thereto,
$R_1$ and $R_3$ are hydrogen,
$R_2$ and $R_4$ are each hydrogen, fluorine or methoxy,
$R_5$, $R_6$, $R_7$ and $R_8$ are methyl, or,
$R_5$ and $R_6$, together with each other, are straight alkylene of 2 to 5 carbon atoms, or
$R_7$ and $R_8$, together with each other, are straight alkylene of 2 to 5 carbon atoms, and
$R_9$ is hydrogen, alkyl of 1 to 3 carbon atoms or phenyl-(alkyl of 1 to 3 carbon atoms).

4. A compound of claim 1, which is N,N-bis-[3-(3,4-dihydro-4,4-dimethyl-1,3-dioxo-2(1H)-isoquinolyl)-propyl]-amine or a non-toxic, pharmaceutically acceptable acid addition salt thereof.

5. A compound of claim 1, which is N-[2-(3,4-dihydro-4,4-dimethyl-1,3-dioxo-2(1H)-isoquinolyl)-ethyl]-N-[3-(3,4-dihydro-7-methoxy-4,4-dimethyl-1,3-dioxo-2(1H)-isoquinolyl)-propyl]-methylamine or a non-toxic pharmaceutically acceptable acid addition salt thereof.

6. A compound of claim 1, which is N-[2-(3,4-dihydro-4,4-dimethyl-1,3-dioxo-2(1H)-isoquinolyl)-ethyl]-N-[3-(3,4-dihydro-4,4-dimethyl-1,3-dioxo-2(1H)- isoquinolyl)-propyl]amine or a non-toxic, pharmaceutically acceptable acid addition salt thereof.

7. A compound of claim 1, which is N,N-bis-[2-(3,4-dihydro-4,4-dimethyl-1,3-dioxo-2(1H)-isoquinolyl)-ethyl]-amine or a non-toxic pharmaceutically acceptable acid addition thereof.

8. A compound of claim 1, which is N-[2-(3,4-dihydro-4,4-dimethyl-1,3-dioxo-2(1H)-isoquinolyl)-ethyl]-N-[4-(3,4-dihydro-4,4-dimethyl-1,3-dioxo-2(1H)-isoquinolyl)-butyl]-amine or a non-toxic pharmaceutically acceptable acid addition salt thereof.

9. An antiarrhythmic pharmaceutical dosage unit composition consisting essentially of an inert pharmaceutical carrier and an effective antiarrhythmic amount of a compound of claim 1.

10. The method of preventing or alleviating cardiac arrythmia in a warm-blooded animal, which comprises perorally, parenterally or rectally administering to said animal an effective antiarrhythmic amount of a compound of claim 1.

* * * * *

UNITED STATES PATENT OFFICE
CERTIFICATE OF CORRECTION

Patent No. 4,031,219   Dated June 21, 1977

Inventor(s) EBERHARD KUTTER; VOLKHARD AUSTEL; WOLFGANG EBERLEIN; JOACHIM HEIDER; WALTER KOBINGER; CHRISTIAN LILLIE; RUDOLF KADATZ It is certified that error appears in the above-identified patent and that said Letters Patent are hereby corrected as shown below:

Col. 5, line 23  delete "and1"

Col. 13, line 3  "[3-83,4-" should read -- [3-(3,4- --

Col. 13, line 15  "diono" should read -- dioxo --

Col. 13, line 28  "70°" should read -- 70° C --

Col. 16, line 27  "1,3-2" should read -- 1,3-dioxo-2 --

Col. 16, line 57  "diomo" should read -- dioxo --

Col. 20, line 66  "500.0" should read -- 5000.0 --

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*